(12) United States Patent
Peak

(10) Patent No.: US 7,364,843 B2
(45) Date of Patent: Apr. 29, 2008

(54) METHOD OF IDENTIFYING TARGET CELL USING TARGET CELL-SPECIFIC VIRUS

(75) Inventor: Sang-hyun Peak, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/187,409

(22) Filed: Jul. 22, 2005

(65) Prior Publication Data

US 2006/0252147 A1  Nov. 9, 2006

(30) Foreign Application Priority Data

Nov. 1, 2004 (KR) ...................... 10-2004-0087800

(51) Int. Cl.
C12Q 1/70 (2006.01)
C12Q 1/66 (2006.01)
C12Q 1/42 (2006.01)
G01N 33/53 (2006.01)
G01N 33/542 (2006.01)

(52) U.S. Cl. .......................... 435/5; 435/7.72; 435/7.9; 435/8; 435/21

(58) Field of Classification Search .................... None
See application file for complete search history.

(56) References Cited

U.S. PATENT DOCUMENTS 6,544,729 B2  4/2003  Sayler et al.

OTHER PUBLICATIONS

Tung, Ching-Hsuan, In Vivo Imaging of B-Galactosidase Activity Using Far Red Fluorescent Switch, Cancer Research, Mar. 1, 2004, vol. 64, p. 1579-1583.*
Muller, Bruno, Recombinant single-chain Fv antibody fragment-alkaline phosphotase conjugate for one-step immunodetection in molecular hybridization, Journal of Immunological Methods, 1999, vol. 227, p. 177-185.*
Hennes, Kilian, Fluorescently Labeled Virus Probes Show that Natural Virus Populations Can Control the Structure of Marine Microbial Communities, Applied and Environmental Microbiology, Oct. 1995, vol. 61, No. 10, p. 3623-3627. PTO-1449 Apr. 10, 2006.*
Doolittle et al., Tracing the interaction of bacteriophage with bacterial biofilms using cluorescent and chromogenic probes, Journal of Industrial Microbiology, 1996, vol. 16, pp. 331-3341.*
Neufeld et al., Combines phage typing and amperometric detection of released enzymatic activity for the specific identification and quantification of bacteria, Analytical Chemistry, 2003, vol. 75, pp. 580-585.*
Voss et al. An integrated vector system for cellular studies of pjhage display-derived peptides. Analytical Biochemistry, Sep. 2002, vol. 308, No. 2, pp. 364-372.*
Liu et al. Bispecific monoclonal antibodies against a viral and an enzyme: utilities in ultrasensitive virus ELISA and phage display technology. Journal of Immunological Methods, Mar. 2003, vol. 274, No. 1-2, pp. 115-127.*
"Fluorescently Labeled Virus Probes Show that Natural Virus Populations Can Control the Structure of Marine Microbial Communities"; Authors: Kilian P. Hennes, et al.; Applied and Environmental Microbiology, vol. 61, No. 10; pp. 3623-3627 (1995).
Korean Intellectual Property Office. Notice to Submit Response for Application No. 10-2004-0087800 Issued May 22, 2006.

* cited by examiner

Primary Examiner—Bruce R. Campell
Assistant Examiner—Sharon Hurt
(74) Attorney, Agent, or Firm—Cantor Colburn LLP

(57) ABSTRACT

Provided is a method of identifying a target cell using a virus. The method includes infecting the target cell with the virus by contacting the virus to the target cell and culturing the target cell to propagate the virus; adding a chromogenic substrate to the resultant cell culture to induce enzyme reaction converting the chromogenic substrate to a chromogenic product; and measuring an optical signal emitted from the chromogenic product, wherein the virus contains in its genome a gene encoding an enzyme capable of converting the chromogenic substrate to the chromogenic product and a gene encoding a ligand allowing the virus to specifically bind with a receptor of the target cell to infect the target cell with the virus.

3 Claims, No Drawings

METHOD OF IDENTIFYING TARGET CELL USING TARGET CELL-SPECIFIC VIRUS

CROSS-REFERENCE TO RELATED PATENT APPLICATION

This application claims priority from Korean Patent Application No. 10-2004-0087800, filed on Nov. 1, 2004, in the Korean Intellectual Property Office, the disclosure of which is incorporated herein in its entirety by reference.

1. Field of the Invention

The present invention relates to a method of identifying a target cell using a virus specifically binding with the target cell and expressing a chromogenic enzyme.

2. Description of the Related Art

There is generally known phage typing for identification of specific bacterial cells using viruses. Phage typing is a classification technique for bacterial strains based on different susceptibilities to attack by bacteriophages. For phage typing, a test culture containing bacterial strains is smeared on an agar plate, different phages are inoculated onto discrete areas of the agar plate and cultured. During the culture, cell lysis by phages produces a clear zone in a cloudy bacterial lawn. In this way, identification of specific cells can be performed by production of a clear zone by viruses. According to phage typing, however, since some phages, each of which is specific to several strains of bacteria, are currently known, identification of a specific bacterial strain based on infection patterns by several phages may be indispensable. In addition, since phage typing is based on detection of a clear zone produced by cell lysis by phages, automated signal detection may be difficult.

Hennes et al. introduced a method of identifying *Vibrio natriegens* (bacterial strain PWH3a) using viruses stained with a cyanin-based nucleic acid-specific dye, i.e., YO-PRO-1 and PO-PO-1 [Applied and Environmental Microbiology 61:3623-3627, 1995]. According to the method, bacterial cells infected with the viruses are detected by fluorescent "halo" around the bacterial cells. However, the method involves a disadvantage that viral nucleic acids, whenever used, must be isolated, stained with a fluorescent dye, and subjected to virus packaging. In addition, since natural viruses with low specificity to specific cells are used, detection of several types of cells may be caused.

The above-described conventional techniques are identification of cells using viruses. In this respect, there is still need to develop a method of identifying target cells using viruses which exhibit very high specificity to the target cells, and once constructed, does not require further staining with a dye.

While searching for solutions to the above-described problems, the present inventors found a method of constructing viruses that exhibit very high specificity to target cells, generate detectable signals when infected into the target cells, and can be used repeatedly, and thus completed the present invention.

SUMMARY OF THE INVENTION

The present invention provides a method of identifying target cells using a virus which exhibits high specificity to the target cells, generates a specific signal, and can be used repeatedly.

DETAILED DESCRIPTION OF THE INVENTION

The present invention provides a method of identifying a target cell using a virus, the method including:

infecting the target cell with the virus by contacting the virus to the target cell and culturing the target cell to propagate the virus;

adding a chromogenic substrate to the resultant cell culture to induce enzyme reaction converting the chromogenic substrate to a chromogenic product; and measuring an optical signal emitted from the chromogenic product, wherein the virus contains in its genome a gene encoding an enzyme capable of converting the chromogenic substrate to the chromogenic product and a gene encoding a ligand allowing the virus to specifically bind with a receptor of the target cell to infect the target cell with the virus.

A virus used in the present invention contains, in its genome, a gene encoding an enzyme capable of converting a chromogenic substrate to a chromogenic product and a gene encoding a ligand allowing the virus to specifically bind with a receptor of the target cell to infect the target cell with the virus. The enzyme-encoding gene is not particularly limited provided that it can convert a substrate to a product emitting a detectable signal. Examples of the enzyme include, but are not limited to, luciferase, peroxidase, beta-galactosidase, and alkaline phosphatase. The ligand as used herein is a substance specifically binding with a receptor on a target cell. The ligand is not particularly limited provided that a ligand-receptor complex can induce the incorporation of a virus into a target cell. The ligand may be a natural or artificial substance.

Selection of a virus with specificity to a target bacterial cell may be performed by a random search, a combinatorial library such as a phage display library, an artificial ligand design, etc. These techniques are well known in the pertinent art. Those of ordinary skill in the art can select an appropriate technique to select or construct viruses with specific ligands to target cells.

According to the present invention, a virus expresses a ligand specifically binding with a target cell, and a chromogenic enzyme, on a surface of a virion or a virus envelope. Therefore, the virus can be specifically infected into the target cell and propagated. The virus thus propagated generates an optical signal by enzyme reaction using a chromogenic substrate. The optical signal can be efficiently used for identification of the target cell.

In the present invention, a chromogenic substrate for a chromogenic enzyme may be luciferin, X-gal, or p-nitrophenylphosphate, but is not limited thereto. The wavelength of a generated optical signal may be changed according to the type of a used chromogenic substrate. Those of ordinary skill in the art can easily determine the wavelength of an optical signal by selecting an appropriate one from currently known chromogenic substrates.

According to an embodiment of the present invention, a chromogenic enzyme is expressed in the form of a fusion protein at a virion or a virus envelope. In addition, a chromogenic enzyme as used herein may also be expressed in a target cell provided that a substrate can pass through a cell membrane. In this case, enzyme reaction converting a substrate to a chromogenic product may be performed in a clear zone formed by cell lysis as well as in a target cell.

In the present invention, a target cell may be selected from bacteria including gram(+) bacteria, gram(−) bacteria, and *Enterobacteria,* yeasts, fungi, plant and animal cells, but is not limited thereto. Examples of the target cell include *E. coli, Mycobacterium tuberculosis, Chlamydia pneumonia, Staphylococci aureus, Pseudomonas aeruginosa, Salmonella typhi, Salmonella paratyphi, Salmonella typhimurium, Citrobacter freundii, Enterobacter cloacae, Shigella* sp., and *Bacillus subtilis.*

A virus as used herein expresses a ligand and a chromogenic enzyme. The virus may be bacteriophage, yeast virus, fungal virus, plant or animal virus, but is not limited thereto. Examples of the virus include, but are not limited to, recombinant viruses of phages T1, T4, T6, T7, λ, M13, R17, and fd specific to *E. coli* and recombinant viruses of phages PBS1 and φ29 specific to *Bacillus subtilis.*

According to the present invention, a chromogenic enzyme, which exists on a virus surface or in a virus, or in the form of a gene, is amplified by propagation after incorporation of a virus into a target cell. The chromogenic enzyme thus amplified converts a plurality of substrates to chromogenic products through enzyme-substrate reaction, leading to secondary amplification of an optical signal. Thus, according to the present invention, an optical signal from a target cell can be amplified by isothermal reaction using a virus instead of thermal cycling reaction, which enables easy identification of the target cell.

A method of the present invention may be performed in a vessel commonly used in the pertinent art, for example, a test tube, a flask, or a culture-containing plate. That is, cells are cultured in a test tube, a flask, or a culture-containing plate and infected with viruses by contact between the cells and the viruses to amplify the viruses. Then, a chromogenic substrate is added to the resultant culture to be converted to a chromogenic product. Finally, predetermined wavelength light is irradiated to the culture by a spectrometer and fluorescence emitted from the culture is measured. A method of the present invention may also be performed in a microchamber or microchannel on Lab-On-a-Chip (LOC) to identify a target cell. For example, a test sample is added to a microchamber containing viruses. If the test sample contains target bacterial cells, the viruses are incorporated into the target bacterial cells and amplified. At this time, the viruses emit an optical signal to be measured by enzyme reaction with a chromogenic substrate in the microchamber. A method of the present invention can identify target cells using an optical signal without labeling of viral nucleic acids and detection of a clear zone formed by cell infection with viruses, and thus, is advantageous for automatic system application.

According to a method of the present invention, the presence of target cells in a sample can be easily detected.

What is claimed is:

1. A method of identifying a target cell using a virus, the method comprising:

infecting the target cell with the virus by contacting the virus to the target cell and culturing the target cell to propagate the virus;

adding a chromogenic substrate to the resultant cell culture to induce enzyme reaction converting the chromogenic substrate to a chromogenic product; and measuring an optical signal emitted from the chromogenic product, wherein, when the optical signal is detected at a predetermined wavelength, it is determined that the target cell is present in the cell culture;

wherein the virus contains in its genome a gene encoding an enzyme capable of converting the chromogenic substrate to the chromogenic product and a gene encoding a ligand allowing the virus to specifically bind with a receptor of the target cell to infect the target cell with the virus, wherein the enzyme is expressed in the form of a fusion protein at a virion surface, wherein the virus is a bacteriophage, and wherein the enzyme-encoding gene is a gene encoding an enzyme selected from the group consisting of peroxidase and alkaline phosphatase.

2. The method of claim 1, wherein the chromogenic substrate is p-nitrophenylphosphate.

3. The method of claim 1, wherein the target cell is a prokaryotic cell.

* * * * *